United States Patent [19]

Rauchschwalbe et al.

[11] Patent Number: 5,149,890
[45] Date of Patent: Sep. 22, 1992

[54] PROCESS FOR THE ISOLATION OF PURE DINITROTOLUENES

[75] Inventors: Günther Rauchschwalbe, Leverkusen; Heinz-Ulrich Blank, Odenthal; Ludwig Deibele, Cologne; Kaspar Hallenberger; Gerhard Ruffert, both of Leverkusen, all of Fed. Rep. of Germany

[73] Assignee: Bayer Aktiengesellschaft, Leverkusen, Fed. Rep. of Germany

[21] Appl. No.: 786,479

[22] Filed: Nov. 1, 1991

[30] Foreign Application Priority Data

Nov. 17, 1990 [DE]  Fed. Rep. of Germany ....... 4036758

[51] Int. Cl.$^5$ ............................................. C07C 205/11
[52] U.S. Cl. .................................... 568/934; 568/935; 568/939; 568/940
[58] Field of Search ................ 568/934, 935, 939, 940

[56] References Cited

U.S. PATENT DOCUMENTS

| | | | |
|---|---|---|---|
| 1,450,675 | 4/1923 | Stine | 568/934 |
| 1,836,212 | 12/1931 | Weiland et al. | 568/940 |
| 2,380,248 | 7/1945 | Acken et al. | 568/940 |
| 2,835,714 | 5/1958 | Nixon et al. | 568/940 |
| 2,868,830 | 1/1959 | Weedman | 568/940 |
| 3,232,999 | 2/1966 | Brogden et al. | 568/940 |
| 3,620,928 | 11/1971 | Miserlis | 568/940 |
| 3,816,551 | 6/1974 | Lee | 568/939 |
| 3,931,347 | 1/1976 | Rosenblatt et al. | 568/934 |
| 3,949,008 | 4/1976 | Rosenblatt et al. | 568/934 |
| 4,102,753 | 7/1978 | Stephenson | 938/940 |
| 4,153,630 | 5/1979 | Ichikawa et al. | 568/752 |
| 4,258,224 | 3/1981 | Ribaudo et al. | 568/935 |
| 4,270,013 | 5/1981 | Priegnitz et al. | 568/940 |
| 4,367,347 | 1/1983 | Sawicki | 568/934 |
| 4,717,778 | 1/1988 | Zinnen et al. | 568/934 |
| 5,019,659 | 5/1991 | Manner et al. | 568/949 |

Primary Examiner—Robert L. Stoll
Assistant Examiner—C. Sayala
Attorney, Agent, or Firm—Sprung Horn Kramer & Woods

[57] ABSTRACT

Pure or substantially enriched 2,4- and 2,6-dinitrotoluene can be isolated from a mixture containing these isomers if such a mixture is distilled under a pressure of 0.5 to 20 mbar at a temperature of 80° to 200° C. with exclusion of reducing conditions.

14 Claims, No Drawings

PROCESS FOR THE ISOLATION OF PURE DINITROTOLUENES

BACKGROUND OF THE INVENTION

The invention relates to a process for the isolation of highly enriched to very pure 2,4- and 2,6-dinitrotoluenes (DNT) from mixtures containing these isomers.

It is known that isomer mixtures consisting of 2,4- and 2,6-DNT in a ratio of about 65:35 to about 85:15 are obtained in the nitration of toluene or o-nitrotoluene; small amounts of in each case about 0.1 to 1% of other isomers (2,5-, 2,3- and 3,4-DNT) are also formed.

In the context of the invention, isolation of the isomers mentioned is to be understood as meaning the obtaining of at least 95% pure isomers, preferably about 99% pure isomers of DNT. 2,6-DNT in particular is obtained in an exceptionally high purity of in many cases 99.5% or more.

Separation of the isomer mixtures which are available industrially in order to isolate enriched or pure isomers is extremely difficult. Processes for separation by various methods of adsorption, for example on zeolites, have been disclosed in the literature (U.S. Pat. No. 4,642,397), it being necessary for the isomer adsorbed selectively onto the zeolite to be desorbed again using another solvent. These processes accordingly require large amounts of organic solvents or mixtures of such solvents (such as, for example, butanol/toluene), which, for reasons of protection of the environment, must be separated off, purified and recycled to the process at great expense. Furthermore, only very dilute solutions can be separated in this manner (according to Example 1 of U.S. Pat. No. 4,642,397 0.5 g of 2,4-DNT and 0.5 g of 2,6-DNT in 27.3 g of mesitylene), which pushes up the volumes of organic solvents required further. Due to these limitations alone, the process described is very expensive and economic utilisation on an industrial scale is prevented.

The separation of 2,4- and 2,6-DNT by melt crystallisation is furthermore known (C.A. 87 (1977), 134 189 y). However (probably because of the small differences in melting points), the separation is not very efficient (melting point of 2,4-DNT: 71° C.; melting point of 2,6-DNT: 69° C.), so that high purities can be achieved only by repeated crystallisation and with the associated high technical expenditure. Furthermore, in this process only the 2,4-DNT can be separated off effectively from the isomer mixture obtainable on an industrial scale; the 2,6-DNT remains enriched in the residue. The technical object imposed of preparing pure 2,6-DNT therefore cannot be achieved with this process.

Attempts to separate 2,4- and 2,6-DNT by treatment with organic solvents have furthermore been disclosed.

In the case of U.S. Pat. No. Patent 3,949,008 (extraction with C5-C8-alkanes, specifically with hexane), only traces of secondary isomers could be removed, while the main isomers could not be separated. In the case of recrystallisation from ethanol or $C_2HCl_3$ (C.A. 95 (1981), 80 328 n), it is only possible to prepare 2,4-DNT in a pure form.

The separation of pure 2,6-DNT from isomer mixtures according to U.S. Pat. No. 2,765,348 is achieved only by recrystallisation of solvents which are unacceptable for industrial hygiene reasons, such as N,N-dimethylaniline or toluidine. In this process, filtration has to be carried out at low temperatures (for example at −10° C.), which requires a high technical expenditure. Since the desired product is obtained in only a poor yield (for example 53%) and moderate purity (for example 97%), this process is not economical to carry out.

Only the 2,4-isomer is obtained in a pure form even by crystallisation from DNT isomer mixtures in sulphuric acid (EP 66,202).

Finally, attempts have been made to treat DNT mixtures with reducing agents, such as $Na_2S_2$ (U.S. Pat. No. 3,931,347), $Na_2SO_3$ (JP 45/9169 (1970); cited in C.A. 73 (1970), 14 438 t) or $N_2H_4$ (JP 56/142,245 (1981); cited in C.A. 96 (1982), 85 228 k). In these processes, small amounts of undesirable position isomers are converted into watersoluble products, but the desired 2,4- and 2,6-isomers are not separated.

The preparation of pure 2,6-DNT has indeed already been described, but is carried out by cumbersome routes, that is to say a) by diazotisation and reduction of 2,6-dinitro-4-amino-toluene (Can. J. Chem. 37 (1959), 2073) or b) by heating 2,6-dinitro-phenylacetic acid (Ann. 379 (1911), 152, in particular 181).

Since 2,6-DNT in particular is a sought-after intermediate product for the preparation of dyestuffs and pigments, pharmaceuticals, plant protection agents, polyurethanes and cosmetic products, it was therefore to be assumed that a simple preparation possibility or possibility for isolating the abovementioned products experts had considered such simple methods possible.

SUMMARY OF THE INVENTION

It has now been found, surprisingly, that the separation of the main isomers (2,4- and 2,6-DNT) can be achieved by distillation in which the 2,6-DNT, which hitherto was accessible in a pure form only with great difficulty, in particular can be obtained in an exceptionally high purity (up to 99.9%). Such a separation by distillation has never been described to date and therefore had to be regarded as impossible - against the background of the numerous other attempts at isomer separation.

DETAILED DESCRIPTION OF THE INVENTION

In fact, there are serious prejudices against such an attempt at separation by distillation. Thus, for vaporisation of dinitrotoluenes, DE-OS (German Published Specification) 3,734,344 recommends that this is carried out by addition of a hot inert carrier gas, since according to this DE-OS (German Published Specification) working with DNT in the gas phase, especially on an industrial scale, has the disadvantage of low volatility and ease of decomposition, which can lead to explosions. The carrier gas in the process of this DE-OS (German Published Specification) supplies most of the energy needed for the vaporisation in this method. Although such a procedure reduces the partial pressure of DNT in the vapour phase, which is necessary for evaporation at ambient pressure, and therefore its exposed to heat, due to the presence of the carrier gas, large amounts of carrier gas are necessary, since the usual carrier gases, such as nitrogen and steam, can be charged only with small amounts of DNT. These large amounts of carrier gas prevent the condensation and mass transfer processes voluminous apparatuses.

Furthermore, for separation of compounds having similar boiling points in a distillation column, these compounds must in principle be vaporised several times (partially) and condensed again (partially) in the various separation stages, an equilibrium being established. Some time is necessarily required for this equilibrium to be established. On the other hand, this time necessary for equilibrium to be established is opposed by the need to keep the residence time of the DNT in the hot zones of an apparatus as short as possible; in the DE-OS (German Published Specification) mentioned, not more than 120 seconds at 150° C. or 2 seconds at 250° C. are consequently allowed for a (single!) vaporisation. From this doctrine, it was not to be expected that column distillation with several vaporisation and condensation processes in the individual separation stages and with residence times which are far above the limits allowed in this DE-OS (German Published Specification) could be possible.

Kirk-Othmer, 3rd edition, volume II, page 360 furthermore states that for safety reasons the liquid DNT in a liquid-phase hydrogenation process must be kept at not more than 100° c. However, the vapour pressure of DNT at this temperature is very low, so that distillation is impossible, especially on an industrial scale. This statement is based on the finding that DNT isomer mixtures are sensitive to heat and tend to undergo vigorous decomposition under appropriate exposure to heat. This has already led to serious accidents (Loss Prevention 8 (1974), 117). The decomposition is evidently determined by a number of influencing factors and depends on the temperature and residence time under such influencing factors; in DTA studies (see Loss Prevention, page 118), decomposition temperatures in the range from 260 to 290° C. were found at heating rates of 2° to 4° C./minute, but lower decomposition temperatures are also mentioned, for example 190° C. after heat treatment for 2 days or 175° C. after heat treatment for 7 days. At the temperatures mentioned, DNT or a mixture of various DNT isomers is liquid. No boiling points are known, even under reduced pressure.

It therefore had to be assumed that the experts did not consider distillation of DNT possible because it would have to lead to explosive decomposition of the DNT.

It is known from the literature mentioned that DNT can be handled within a stability criterion defined by the residence time and temperature, for example under 23 days at 150° C., under 7 days at 175° C. or under 2 days at 190° C., before vigorous decomposition occurs (Loss Prevention, page 120). In our own experiments, however, the values mentioned proved to be poorly reproducible. Using industrially available and therefore contaminated starting goods in particular, pairs of values for the temperature and heat treatment time which indicated significantly lower heat stabilities of such DNT mixtures were again and again found. This has so far made industrial distillation of industrial DNT mixtures impossible for safety reasons.

A process has been found for the isolation of pure 2,4-and 2,6-dinitrotoluene, which is characterised in that a mixture containing these isomers is distilled under a pressure of 0.5 to 20 mbar at a temperature of 80° to 200° C. with exclusion of reducing conditions.

The process according to the invention results in a very highly enriched 2,4-isomer (at least 95%) as the bottom product and a very pure 2,6-isomer (at least 99%) as the top product. It is particularly surprising that the two very similar isomers can be separated by distillation with low reflux ratios, low residence times in the column resulting, which in spite of the safety aspects being considered, allow efficient separation of the two isomers mentioned.

It is an important feature of the process according to the invention that the separation by distillation must be carried out such that the isomer mixture to be separated is handled with exclusion of reducing conditions. Reducing conditions which must be excluded according to the invention occur, for example, a) due to the presence of reduced by-products, which originate, for example, from exposure to heat or from treatment with reducing reagents for removal of certain isomers (see the abovementioned literature) or for removal of discoloring oxidation products which are formed during nitration of toluene or nitrotoluene under the influence of heat; or b) due to the presence of traces of acid of industrial origin together with reducing apparatus components (for example iron); or c) also due to contact with alkalis, which can already cause the formation of reduced compounds at about 100° C., which is known, for example, from the structurally related case of 2-nitrotoluene-4-sulphonic acid (German Patent Specification 138,188 (1900)). This is in agreement with the observation that an industrial DNT mixture which contains 2,4- and 2,6-DNT in a ratio of 65:35 shows a highly exothermic decomposition during differential thermal analysis (DTA) at a heating rate of 0.05° C./minute only at from 215° C., while a high exothermicity is already observed at from 130° C. under the same conditions if the DNT contains small amounts of toluylenediamine. These conditions described last exist when DNT is converted into toluylenediamine in liquid-phase hydrogenation (compare the abovementioned literature of Kirk-Othmer). The upper temperature limit of 100° C. to be observed during liquid-phase hydrogenation, as described above, is due to the presence of the already reduced substances, which reduce the stability of the DNT; this relationship has not previously been recognised, but has been found and investigated in connection with the present invention.

The exclusion of reducing conditions can be achieved by various measures. The presence of reducing agents can thus be excluded from the beginning. The isomer mixtures present can furthermore be freed from reducing concomitant substances by suitable measures. For this, for example, the starting goods are first washed with acid, in order to remove reduced by-products (mainly amines). They are then washed with a little alkali in order to remove residues of acid, which would lead to corrosion and reduction. Thereafter, they are washed with a large quantity of water in order to remove the residues of alkali with certainty, which could cause the formation of reduced compounds during subsequent heating. An industrial DNT mixture is moreover handled in corrosion-resistant apparatuses, to exclude the formation of reduced compounds from the beginning. Examples of corrosion-resistant materials which may be mentioned are stainless steel, enamelled steel, glass or Hastelloy. It is also possible to use other corrosion-resistant materials, such as are known to the expert.

It has furthermore proved to be advantageous to check every batch intended for distillation analytically for residues of acid or alkali and for its heat stability.

The DNT mixture is preferably evaporated under gentle conditions, it being particularly advantageous to use a falling film evaporator, since it is possible to achieve only a low residence time in the evaporator in this apparatus under good heat transfer. It is furthermore advantageous to use heat transfer liquids having a boiling point below the decomposition point of the DNT mixture as the heating agent in an evaporator. Such heat transfer liquids can be, for example, dichlorobenzene, particularly preferably m-dichlorobenzene.

The evaporated DNT mixture is then passed into the central region of a continuously operating distillation column which consists of a stripping and concentrating part and is fitted with baffles or packing with the lowest possible pressure loss. The separation is carried out at a reflux ratio of reflux: withdrawal = 1-10:1, preferably 2-5:1, particularly preferably 2.5-3.5:1. According to the invention, the pressure in the column is 0.5 to 20 mbar, preferably 1 to 15 mbar. The temperature in the distillation column is, according to the invention, 80° to 200° C., depending on the pressure, preferably 100° to 180° C. and particularly preferably 90° to 170° C.

Measurement of the bottom temperature, where the temperature is highest and therefore closest to the safety limits of the process, preferably serves as a control.

The isolation in the distillation column is controlled in the context of the conditions mentioned, in particular by adjusting the reflux ratios, so that the DNT isomers are obtained in purities of about 90% to 99.99%.

The distillate (2,6-DNT) is condensed and removed from the apparatus in liquid form.

The pure DNTs thus obtained are suitable as intermediate products and for this purpose are in general further processed by catalytic hydrogenation to pure diaminotoluenes, which in turn have the abovementioned industrial use.

The process according to the invention for the isolation of the DNT isomers by distillation is particularly surprising if our own finding that the structurally very similar diaminotoluene mixtures, which are obtained from the DNT mixtures by reduction, cannot be separated in the manner described is taken into account.

EXAMPLE 1

Distillation column (500 mm diameter, 1.80 m in the concentrating part, 1 m height in the stripping part, with Sulzer-BX packing, 6-7 separation stages per m, made of stainless steel) at a feed of 100 kg per hour of dinitrotoluene (DNT) mixture (65% of the 2,4- and 35% of the 2,6-isomer) at a reflux ratio of 3:1, a bottom temperature of 140° to 145° C., an overhead temperature of 94° C., a pressure in the bottom of 4.5 mbar and a pressure . at the top of 1 mbar. The 2,6-DNT distilled over at the top of the concentrating part in a purity of 99%, while the 2,4-DNT was removed from the bottom in a purity of about 95-97%.

EXAMPLE 2

Distillation was carried out in a continuously operated distillation column (500 mm diameter, 2.5 m height in the concentrating part, 1.5 m height in the stripping part, with Sulzer-BX packing, of corrosion-free steel) at a feed of 100 kg/hour of the DNT mixture as in Example 1 and a reflux ratio of 3:1, a bottom temperature of 170° C., an overhead temperature of 132° C., a pressure in the bottom of 13 mbar and a pressure at the top of 5 mbar. The 2,6-DNT distilled over at the top of the column in a purity of 99.9%, while the 2,4-DNT was removed from the bottom in a purity of 97-98%.

What is claimed is:

1. A process for the isolation of pure 2,4- and 2,6-dinitrotoluene, wherein a mixture containing these isomers is distilled in a distillation column having a central region, under a pressure of 0.5 to 20 mbar and at a temperature of 80° to 200° C. with exclusion of reducing conditions.

2. The process of claim 1, wherein the pressure is 1 to 15 mbar.

3. The process of claim 1, wherein the temperature is 100° to 180° C.

4. The process of claim 3, wherein the temperature is 90° to 170° C.

5. The process of claim 1, wherein the temperature to be controlled is that of the bottom of the column.

6. The process of claim 1, wherein the dinitrotoluene mixture to be separated is evaporated in a short-time evaporator and is fed into the central region of the distillation column in the form of a vapour.

7. The process of claim 6, wherein the short-time evaporator is a falling film evaporator.

8. The process of claim 6, wherein the short-term evaporator is heated with the aid of a heat transfer liquid, the boiling point of which is below the decomposition point of the dinitrotoluene mixture.

9. The process of claim 1, wherein mixtures which contain the 2,4- and 2,6-isomer in a ration of 65:35 to 85:15 are employed.

10. The process of claim 1, wherein a reflux ratio of reflux:withdrawal = 1-10:1 is established.

11. The process of claim 10, wherein a reflux ratio of 2-:1 is established.

12. The process of claim 11, wherein a reflux ratio of 2.5-3.5:1 is established.

13. The process of claim 1, wherein the dinitrotoluene mixture to be separated is treated a) with acid, b) with alkali until the acid has been removed and c) with water until the alkali has been removed 14. The process of claim 1, wherein the distillation is carried out in a corrosion-resistant apparatus.

* * * * *

UNITED STATES PATENT AND TRADEMARK OFFICE
CERTIFICATE OF CORRECTION

PATENT NO. : 5,149,890

DATED : September 22, 1992

INVENTOR(S) : Rauchschwalbe et al

It is certified that error appears in the above-identified patent and that said Letters Patent is hereby corrected as shown below:

Col. 6 line 45    Delete " 2-:1 " and substitute -- 2-5:1 --

Signed and Sealed this

Fifteenth Day of March, 1994

Attest:

BRUCE LEHMAN

Attesting Officer    Commissioner of Patents and Trademarks